(12) United States Patent
Chiu et al.

(10) Patent No.: US 10,391,149 B2
(45) Date of Patent: Aug. 27, 2019

(54) METHODS TO ENHANCE NERVE REGENERATION UTILIZING NEURAL STEM CELLS AND IL12P40

(71) Applicant: National Health Research Institutes, Zhunan Township (TW)

(72) Inventors: Ing-Ming Chiu, Zhunan Town (TW); Ya-Hui Chi, Zhunan Town (TW); Don-Ching Lee, Zhunan Town (TW)

(73) Assignee: NATIONAL HEALTH RESEARCH INSTITUTES, Zhunan Township (TW)

( * ) Notice: Subject to any disclaimer, the term of this patent is extended or adjusted under 35 U.S.C. 154(b) by 0 days.

(21) Appl. No.: 15/504,301

(22) PCT Filed: Aug. 14, 2015

(86) PCT No.: PCT/CA2015/050775
§ 371 (c)(1),
(2) Date: Feb. 15, 2017

(87) PCT Pub. No.: WO2016/023130
PCT Pub. Date: Feb. 18, 2016

(65) Prior Publication Data
US 2017/0224776 A1    Aug. 10, 2017

Related U.S. Application Data (60) Provisional application No. 62/037,612, filed on Aug. 15, 2014.

(51) Int. Cl.
A61K 9/00 (2006.01)
A61K 35/30 (2015.01)
A61K 38/18 (2006.01)
A61K 38/20 (2006.01)
A61K 35/28 (2015.01)
A61K 35/50 (2015.01)

(52) U.S. Cl.
CPC .......... *A61K 38/208* (2013.01); *A61K 9/0019* (2013.01); *A61K 9/0024* (2013.01); *A61K 35/28* (2013.01); *A61K 35/30* (2013.01); *A61K 35/50* (2013.01); *A61K 38/185* (2013.01); *A61K 38/1825* (2013.01); *A61K 38/1858* (2013.01)

(58) Field of Classification Search
CPC combination set(s) only.
See application file for complete search history.

(56) References Cited

FOREIGN PATENT DOCUMENTS

EP    1374898 B1 *  6/2007

OTHER PUBLICATIONS

Ehtesham et al., Cancer Research, 62:5657-5663, Oct. 2002.*
Fleischmann et al., Journal of Interferon & Cytokine Research vol. 19, No. 8, 1999; abstract only.*
Orbach et al., Multiple Sclerosis Journal, vol. 20(1) 35-42, 2014.*
Hsu et al., Biomed J., 36:98-105, 2013.*
Lin et al. Neuroscience Letts., 278:129-132, 2000.*
Ha et al., J Immunol., 163:2902-2908, 1999. (Year: 1999).*

* cited by examiner

Primary Examiner — Kimberly Ballard
Assistant Examiner — Stacey N MacFarlane
(74) Attorney, Agent, or Firm — Chen Yoshimura LLP (57) ABSTRACT The present application provides a composition and methods to enhance nerve regeneration utilizing at least one component of neural stem cells or IL12p40. The composition comprises neural stem cells and a neurotrophic factor, which is constructed by IL12p40 as at least one subunit. The methods to enhance nerve regeneration comprise providing a nerve regeneration composition comprising a neurotrophic factor containing IL12p40 as at least one subunit to a subject. The composition of the methods can further comprise neural stem cells.

5 Claims, 10 Drawing Sheets

FIG. 1

|   | A | B | C | D | E | F | G | H |
|---|---|---|---|---|---|---|---|---|
| 1 | POS | POS | NEG | NEG | Blank | Eotaxin | Fas Ligand | FGF2 |
| 2 | POS | POS | NEG | NEG | Blank | Eotaxin | Fas Ligand | FGF2 |
| 3 | G-CSF | GM-CSF | IFNγ | IGF-II | IL1α | IL1β | IL12p40 | IL12p35 |
| 4 | G-CSF | GM-CSF | IFNγ | IGF-II | IL1α | IL1β | IL12p40 | IL12p35 |
| 5 | IL13 | IL6 | IL9 | Leptin | MCP1 | M-CSF | MIG | PF-4 |
| 6 | IL13 | IL6 | IL9 | Leptin | MCP1 | M-CSF | MIG | PF-4 |
| 7 | TIMP-1 | TIMP-2 | TNFα | TPO | VEGF | Blank | Blank | POS |
| 8 | TIMP-1 | TIMP-2 | TNFα | TPO | VEGF | Blank | Blank | POS |

FIG. 4 (continuous)

FIG. 6 (continuous)

METHODS TO ENHANCE NERVE REGENERATION UTILIZING NEURAL STEM CELLS AND IL12P40

CROSS-REFERENCE TO RELATED APPLICATION

This application claims priority to U.S. Provisional Patent Application No. 62/037,612, filed on Aug. 15, 2014, the disclosure of which is hereby incorporated by reference in its entirety.

BACKGROUND OF THE INVENTION

1. Field of the Invention

The present application relates to a composition and methods to enhance nerve regeneration utilizing neural stem cells and IL12p40.

2. Description of the Related Art

Severed peripheral nerve injury causes a reduction in motor and sensory neuron activities, and degeneration of nerve fibers and the surrounding tissues. The regeneration of injured peripheral nerve is a multiplex process, with Wallerian degeneration (WD) being the most elementary reaction and Schwann cells playing an important role (Ren Z. et al., *Reviews in the Neurosciences* 2012, 23:135-143). WD creates a microenvironment for regeneration of surviving neurons and benefits functional recovery (Navarro X. et al., *Progress in Neurobiology* 2007, 82:163-201.). The control of WD involves the existence of Schwann cells, the secretion of neurotrophic factors, and special extracellular matrix that acts as a scaffold for neural cells (Gaudet A. D. et al., *Journal of Neuroinflammation* 2011, 8:110; Kehoe S. et al., *Injury* 2012, 43:553-572.).

Nerve conduits provide mechanical support and direct axonal sprouting between the injured nerve stumps. Conduits have been shown to retain neurotrophic factors secreted from or recruited by the damaged cells (Kehoe S. et al, *Injury* 2012, 43:553-572.) and prevent ingrowth of fibrous tissue at the injury site. Recent studies reveal that implantation of neural stem cells (NSCs) in conduits promote regeneration of injured peripheral nerves (Zhang H. et al., *Journal of Translational Medicine* 2008, 6:67; Shi Y. et al., *Acta Oto-Laryngologica* 2009, 129: 906-914.).

The promotion of nerve regeneration may depend on the ability of implanted NSCs to differentiate into Schwann cells, to secrete neurotrophic factors per se, or create a microenvironment to enrich neurotrophic factors from milieu, and to assist in myelination (Ren Z. et al., *Reviews in the Neurosciences* 2012, 23:135.443). However, the nature of cytokines or growth factors that are involved in this process is not clear. The molecular mechanism for the Schwann cell differentiation of the implanted NSCs into newly regenerated axons is also not well established.

In this study, it is an aim to identify factors that are involved in NSCs-mediated nerve regeneration and functional recovery. Using a protein antibody array, we searched for protein level differences in a mouse sciatic nerve injury model using conduits with or without NSCs. The levels of IL12p80 (the bioactive homodimer form of IL12p40) (Heinzel F. P. et al., *Journal of Immunology* 1997, 158:4381-4388) in these conduits were nearly two-fold higher than those in conduits without NSCs. Implantation of NSCs with nerve conduit and IL12p80 improved motor function in a sciatic nerve injury mouse model.

Administration of IL12p80 further enhanced nerve regeneration as evidenced by the increased diameter in the regenerated nerve, up to 4.5-fold thicker than the Conduit only group at the medial section of the regenerated nerve and improved nerve conduction. This is showed that IL12p80 induced the neuroglia differentiation of mouse NSCs in vitro through phosphorylation of signal transducer and activator of transcription 3 (Stat3). The neuroglia comprises astroglia, oligodendrocytes, and Schwann cells as reported by Kettenmann and Verkhratsky (Kettenmann H, Verkhratsky A, *Fortschritte der Neurologie-Psychiatrie* 2011, 79:588-597.).

SUMMARY

The present application provides a composition for nerve regeneration comprising neural stem cells and a neurotrophic factor, which is constructed by IL12p40 as at least one subunit.

The present application provides a composition for nerve regeneration comprising neural stem cells, a neurotrophic factor, which is constructed by IL12p40 as at least one subunit, and a nerve regeneration enhancing element.

The present application further provides a composition for nerve regeneration comprising neural stem cells, a neurotrophic factor, which is constructed by IL12p40 as at least one subunit, and a nerve conduit for carrying at least one of the neural stem cells and the neurotrophic factors.

The present application provides a method for regenerating nerve, comprising providing a nerve generation composition comprising a neurotrophic factor containing IL12p40 as at least one subunit to a subject.

The present application further provides a method for regenerating nerve, comprising providing a nerve regeneration composition comprising neural stem cells and a neurotrophic factor containing IL12p40 as at least one subunit to a subject.

BRIEF DESCRIPTION OF THE DRAWINGS

FIG. 3 is schematic diagrams illustrating the comparative analysis of functional assessment using SFI and Rotarod tests in NSCs transplant with or without IL12p80. On the eighth week after surgery, mice of the Conduit+NSC and Conduit+NSC+mIL12 group showed significantly higher SFI scores than the Conduit only group (A). In the Rotarod test, mice of the Conduit+NSC and Conduit+NSC+mIL12 group showed greater ability of walking and balance than the Conduit only group (B). These data indicated that the Conduit+NSC+mIL12 group showed statistically more significant results (**p<0.01) than the group without IL-12p80 (*p<0.05) in functional assessment of both SFI and Rotarod analyses. Data are presented as mean±SEM (In SFI, n=3 in the Conduit to only group, n=3 in the Conduit+NSC group, and n=4 in the Conduit+NSC+mIL12 group. In the Rotarod test, n=7 in the Conduit only group, n=5 in the Conduit+NSC group, and n=8 in the Conduit+NSC+mIL12 group).

FIG. 4 illustrates the H&E staining and immunohistochemistry of regenerated sciatic nerve sections. (A-C) The sections of newly regenerated axon were stained with hematoxylin and eosin and "P" and "D" indicate the ends of residual nerve ("P" is 1.0 mm from the proximal end of conduit and "D" is 3.0 mm distal from "P"). The Conduit only group (A) showed less integration of regenerated axon than the Conduit+NSC group (B) and Conduit+NSC+mIL12 group (C). Furthermore, we verified the characteristics of regenerating nerve using immunohistochemistry staining with anti-neurofilament 200 antibody (NF200, a marker of nerve fiber) and anti-protein zero antibody (PZO, a marker of myelinated Schwann cells). The staining results showed the failure of axon regeneration in the Conduit only group (D). We could observe that myelinated Schwann cells (PZO positive cell) coupling nerve fiber (NF200 positive cell) existed in the medial region of conduits in the Conduit+NSC (E) and more so in the Conduit+NSC+mIL12 groups (F). The relative locations of D, E, and F are shown in dotted squares in A, B, and C, respectively. The quantitative results of regenerated nerve diameter at different sites are shown in (G), where the Proximal site indicated is 1.0 mm from the proximal end of the conduit, the Distal site indicated is 3.0 mm from the Proximal site, and the Medial site indicated is central between the Proximal and Distal sites (n=3 in the Conduit only group, n=4 in the Conduit+NSC group, and n=3 in the Conduit+NSC+mIL12 group). The schematic diagram of regeneration of different treatment groups is shown in (H). Scale bars in (A), (B), and (C) are 1 mm, (D), (E), and (F) are 100 µm. Statistical differences are shown as *p<0.05 and **p<0.01.

FIG. 8 illustrates that the IL12p80 induces phosphorylation of Stat3 in NSCs. The phosphorylation levels of Stat3 in Y705 and S727 sites (pStat3) in control medium (Control) or differentiation medium containing human IL12p80 (hIL12) or mouse IL12p70 (mIL12) at different time points (Sphere, 0 min, 15 min, 30 min, 1 h, 2 h, 4 h, and 8 h) were determined by Western blotting analyses. The results show that the levels of pStat3 peaked at 15 minutes when cultured with IL12p80. The total Stat3 and α-Tubulin were used as controls.

DETAILED DESCRIPTION OF THE EMBODIMENTS

In the present application, a composition for nerve regeneration comprises NSCs and a neurotrophic factor, which is constructed by IL12p40 as at least one subunit. In some embodiment, IL12p40 has a protein sequence shown as NCBI Accession No.: NM_008352 (Mouse) or 1F42_A (Human).

The neurotrophic factor can be a monomer of IL12p40, or a homodimer or a heterodimer, wherein at least one subunit is IL12p40. In embodiments, the neurotrophic factor can be a heterodimer of IL12p40, a homodimer of IL12p40, a trimer of IL12p40, a tetramer of IL12p40 or any combination thereof. In an embodiment, the homodimer can be an IL12p80. In embodiments, the heterodimer can be an IL12p70.

In the present application, the NSCs of the composition for nerve regeneration can be characterized as brain cells that are positive for CD133 and GFAP, or characterized as F1B-GFP$^+$ cells.

The present application provides a composition further comprising a nerve regeneration enhancing element. The nerve regeneration enhancing element comprises cells, growth factors, and any combination thereof. In embodiments, the nerve regeneration enhancing element can be Schwann cells, mesenchymal stem cells (MSCs), adipose-derived stern cells (ADSCs), amniotic fluid stem cells (AFSCs), induced neurons (iNs), induced neural stem cells (iNSCs), or cell that are derived from induced pluripotent stem cells (iPSCs).

In some embodiment, the nerve regeneration enhancing element can be fibroblast growth factor 1 (FGF1), fibroblast growth factor 2 (FGF2), platelet derived growth factor (PDGF), brain derived neurotrophic factor (BDNF), glial cell derived neurotrophic factor (GDNF), nerve growth factor (NGF), and any combination thereof.

In an embodiment, the composition can further comprise a nerve conduit for carrying at least one of the NSCs and the neurotrophic factors. In some embodiments, the nerve conduit further carries the nerve regeneration enhancing elements.

The present also provide a method for regenerating nerve, comprising providing a nerve regeneration composition comprising neural stem cells and a neurotrophic factor containing IL12p40 as at least one subunit to a subject. In some embodiments, the nerve regeneration composition can further comprise NSCs. In embodiment, the nerve regeneration composition can be contained in a nerve conduit. In embodiments, the nerve conduit is implanted in a target nerve or a tissue around the target nerve.

The neurotrophic factor can be a monomer of IL12p40, a heterodimer of IL12p40, a homodimer of IL12p40, a trimer of IL12p40, a tetramer of IL12p40 or any combination thereof. In some embodiments, the neurotrophic factor is IL12p80.

The subject is a mammalian. In an embodiment, the mammalian can be mice or humans. In the present application, the composition can be provided by injection, implantation, transdermal route, and/or oral administration.

EXAMPLES

Materials and Methods
Sequence of IL12p40

The protein sequence of IL12p40 is shown as NCBI Accession No.: NM_008352 (Mouse) or 1F42_A (Human), which are available from the website of National Center for Biotechnology Information (www.ncbi.nlm.nih.gov).

Cell Culture and NSCs Isolation.

Mouse NSCs isolation and cell culture were performed as described in two previous publications (Hsu Y. C. et al., *Developmental Dynamics* 2009, 238:302-314; Lee D. C. et al., *Molecular and Cellular Neurosciences* 2009, 41:348-363; the two publications are incorporated by references in theirs entirety.)

KT98/F1B-GFP cells were cultured in Dulbecco's modified Eagle's medium (DMEM)/F12 (1:1) containing 10% fetal bovine serum (FBS), 1% penicillin/streptomycin, and 500 µg/ml G418 (Merck, USA). For NSCs isolation, The GFP-positive KT98/F1B-GFP (KT98/FIB-GFP+) cells were sorted using FACSAria cell sorter (BD Bioscience) and cultured in neurosphere formation medium (DMEM/F12 containing 1×B27 (Gibco), 20 ng/ml EGF (PeproTech Inc.), 20 ng/ml FGF2 (PeproTech Inc.), 2 µg/ml heparin (Sigma), and 500 µg/ml G418) for 7 days, which induced KT98/F1B-GFP+ neurosphere formation. Then KT98/F1B-GFP+ neurosphere-derived single cells were used in subsequent animal experiments and cell differentiation assays. All cells were cultured at 37° C. with 5% $CO_2$.

Animal Surgery: Sciatic Nerve Injury and Conduit Implantation.

In the present application, all animal experimental procedures followed the ethical guidelines and were approved by the Institutional Animal Care and Use Committee (IACUC) of National Health Research Institutes (Protocol No. NHRI-IACUC-101067A). FVB mice (8-10 weeks old) were used for animal experiments and were maintained in National Health Research Institutes (NHRI) Animal Center. Before surgery, mouse was anesthetized by 5% isoflurane (Halocarbon) air inhalation and anesthetization was maintained by 2% isoflurane air inhalation during surgery. In sciatic nerve injury surgery, a 3 mm mouse sciatic nerve segment was excised with microscissors. For the surgical implantation of nerve conduits, the poly(L-lactic acid) (PLA) conduit was used, as previously described (Hsu S. H. et al., *Artif Organs* 2009, 33:26-35; the publication is incorporated by reference in its entirety.)

The 5 mm conduit with or without NSCs and/or mouse IL12p80 were implanted into the sciatic nerve injury site. Proximal and distal end nerves of the sciatic nerve injury site were anchored into the conduit with 1 mm residual nerve using 6-0 nylon microsutures. Mice which did not undergo sciatic nerve injury were defined as the Sham control group (n=3).

The surgical implantation groups included a Conduit only group (n=8), Conduit+NSC group (n=8), and a Conduit+NSC+mIL12 group (n=8). In the Conduit only group, conduits were filled with 5 µl matrigel (BD Bioscience)/phosphate buffer saline (PBS) mixture (1:1). For the Conduit+NSC group (n=8), conduits were filled with 5 µl matrigel/PBS mixture (1:1) with $1\times10^6$ NSCs. In the Conduit+NSC+mIL12 group (n=8), conduits were filled with 5 µl matrigel/PBS mixture (1:1) with 1×106 NSCs and 100 ng mouse IL12p80 (BioLegend).

Functional Assessments: Walking Track Analysis and Rotarod Test.

Walking track analysis was performed using the Treadmill/TreadScan system (CleverSys) and presented as sciatic functional index (SFI) every week after surgery. The formula for SFI is as follows:

$$SFI = -38.3\times\left(\frac{EPL-NPL}{NPL}\right)+109.5\times\left(\frac{ETS-NTS}{NTS}\right)+13.3\left(\frac{EIT-NIT}{NIT}\right)-8.8$$

SFI calculation was according to normal (N) and experimental (E) feet where PL indicated the length of the footprint (the longitudinal distance between the tip of the longest toe and the heel), TS indicated the total toe spread (the cross-sectional distance between the first and fifth toes) and IT indicated the intermediate toe spread (the cross-sectional distance between the second and the fourth toes). Adult FVB mice were used to obtain the normal walking video (total 1500 frames were collected in a complete walking period of one mouse) and these image data were used to calibrate the TreadScan software (10-12 outlines of each step were sufficient to train the software for identification of the paw position). After calibration, the well-established program is used to exclude abnormal walking status and irregular toe spread during an entire walking period of sciatic nerve injury mice.

The Rotarod test was executed by RT series Rotarod Treadmill (SINGA) at the fourth and eighth week after surgery. In the Control group, mice were defined as without nerve dissection and muscle injury (n=8 at the fourth week and n=8 at the eighth week). Before formal data collection, each mouse ran on the rotating rod for three times each at 10 rpm, 12 rpm, and 15 as a pre-test course. For data collection, mice ran on the rotating rod six times at 20 rpm. The maximal recording time was 120 seconds.

Protein Array.

Protein samples were extracted from the implanted conduits using 1×RIPA buffer [50 mM HEPES, pH 7.3, 150 mM NaCl, 2 mM EDTA, 20 mM β-gylcerophosphate, 0.1 mM $Na_3VO_4$, 1 mM NaF, 0.5 mM DTT, and 0.5% NP-40] containing 1× protease inhibitor cocktail (Roche). 100 µg of protein sample was used in the mouse angiogenesis protein antibody array (RayBiotech) analysis, which followed the manufacturer's protocol. Protein levels were detected with chemiluminescence methods.

Neural Differentiation Assay.

Single cells were dissociated from the neurospheres using 1× HyQTase (Hyclone). $2\times10^3$ cells were seeded onto Poly-D-Lysine (BD Bioscience)-coated chamber slides with neural differentiation medium (DMEM/F12 containing 2% FBS) supplemented with or without inducing factors. For CNTF+T3 group, neural differentiation medium were supplemented with 50 ng/ml CNTF and 10 ng/ml T3. For hIL12 and mIL12 group, neural differentiation medium were supplemented with 100 ng/ml human IL12p80 and mouse IL12p80, separately. For CNTF+T3+hIL12 group, neural differentiation medium were supplemented with 50 ng/ml CNTF, 10 ng/ml T3 and 100 ng/ml human IL12p80. For CNTF+T3+mIL12 group, neural differentiation medium were supplemented with 50 ng/ml CNTF, 10 ng/ml T3 and 100 ng/ml mouse IL12p80. CNTF, T3, and human IL12p80 were purchased from PeproTech. Culture media was replaced every three days.

Immunofluorescence Staining.

Cells were grown on chamber slides (Nunc, Naperville, Ill., USA) at 37° C. with 5% $CO_2$. For immunofluorescent staining, cells were washed with PBS and fixed with 4% (v/v) paraformaldehyde (PFA; Electron Microscopy Sciences) in PBS for 15 min at room temperature. Cells were then permeated with 0.1% (v/v) Triton X-100 in PBS for 15 min at room temperature. Cells were then blocked with blocking solution (1% BSA in 1×PBS) at RT for 1 hour, and followed by incubation with specific primary antibody for 1 hour at room temperature. In the present application, the differentiation capacity is verified by using immunofluorescence staining with mouse monoclonal antibody against galactocerebroside (Galc, 1:1000, Millipore), rabbit polyclonal antibody to oligodendrocyte specific protein (OSP, 1:1000, Abcam), and chicken polyclonal antibody to myelin protein zero (PZO, 1:1000, GeneTex). Subsequently, the cells were incubated with rhodamine-conjugated secondary antibody (Millipore, Billerica, Mass., USA) for 1 hour at room temperature. All sections were stained for nuclei with 2-(4-Amidinophenyl)-6-indolecarbamidine dihydrochloride (DAPI) (Molecular Probes), and observed under a fluorescent microscope (Olympus, Tokyo, Japan). Galc/DAPI, OSP/DAPI and PZO/DAPI double-positive cells were counted and normalized to the Control group.

Western Blotting.

Rabbit polyclonal antibody against glial fibrillary acidic protein (GFAP, 1:1000; Abcam), rabbit polyclonal antibody against oligodendrocyte specific protein (OSP, 1:4000; Abcam), chicken polyclonal antibody against myelin protein zero (PZO, 1:4000; GeneTex), and rabbit polyclonal antibody against α-tubulin (α-tubulin, 1:8000 diluted; GeneTex) were used to detect the corresponding protein levels by the immunoblotting method in differentiated cells, which were isolated from neurospheres and cultured with neural differentiation medium with or without inducing factors (Table 1) for 7 days. Protein samples from differentiated cells were harvested by 1×RIPA Lysis Buffer (Millipore, Billerica, Mass., USA) supplemented with 1× protease inhibitor cocktail (Roche).

Mouse monoclonal antibody against Stat3 (1:1000; Cell Signaling), rabbit polyclonal antibody against pStat3-Y705 site (1:1000; Cell Signaling), rabbit polyclonal antibody against pStat3-S727 site (1:1000; Cell Signaling), and rabbit polyclonal antibody against α-tubulin (α-tubulin, 1:8000 diluted; GeneTex) were used to analyze Stat3 phosphorylation status in mouse NSCs after IL12p80 treatment. Single cells were isolated from neurospheres and experimental signal cells were harvested by centrifugation for 3 minutes and cell lysates were extracted at different time points (Sphere, 0 min, 15 min, 30 min, 1 h, 2 h, 4 h, and 8 h). Thus, at time point "0 min," cells had been in the presence of with IL12p80 for 3 minutes during the centrifugation period. Cell lysates were analyzed using Western blotting.

The protein concentration of each sample was determined by protein assay dye reagent (Bio-Rad Laboratories). Equal amounts of protein samples were size fractionated by sodium dodecyl sulfate-polyacrylamide gel (SDS-PAGE) and then transferred to polyvinylidene fluoride (PVDF) membranes (Amersham). Thereafter, membranes were blocked in 5% bovine serum albumin (Bio Basic, Markham Ontario, Canada) blocking buffer for 1 hour at room temperature. The membranes were then incubated with specific primary antibodies in 5% bovine serum albumin blocking buffer followed by incubation with corresponding HRP-conjugated secondary antibodies (1:10000) (Millipore). Protein levels were revealed using ECL reagents (Millipore) and X-ray films with α-tubulin as an internal control. Immunoreactive bands of three individual experiments were quantitated by ImageJ software and normalized to the Control group.

Compound Muscle Action Potential Measurement.

Compound muscle action potential was recorded and analyzed with BIOPAC MP36 and BIOPAC BSL 4.0 software (BIOPAC system Inc.). The stainless steel electrode was 0.22 mm in diameter. Stimulating electrodes were placed in the sciatic notch and recording electrodes were placed in the gastrocnemius muscle (approximately 2 cm from the sciatic notch). Stimulation voltage was 6 volts, stimulus duration was 0.1 millisecond, and acquisition length was 200 milliseconds. Distances were measured with a vernier caliper, and skin temperature was maintained at 36° C. in a room maintained at a constant temperature of 25° C.

Hematoxylin and Eosin (H&E) Staining and Immunohistochemistry Staining.

Implanted conduits were collected on the eighth week after surgery. In briefly, the implanted conduits were fixed with 4% PFA at 4° C. overnight. Fixed samples were dehydrated using 30% sucrose in 1×PBS at 4° C. overnight. Samples were embedded in Tissue-Tek O.C.T. (Sakura, Netherlands), then frozen in liquid nitrogen and stored at −80° C.

For Hematoxylin and Eosin (H&E) and immunohistochemistry staining, cryo-embedded nerve conduits were sliced at 10 μm onto slides using a cryostat microtome (MICROM HM550). Immunohistochemistry staining was performed by specific antibody: rabbit polyclonal antibody against neurofilament 200 (NF-200, 1:500, marker of nerve fiber) and chicken polyclonal antibody against myelin protein zero (PZO, 1:500, marker of myelinated Schwann cell). After PBS washing, samples were incubated with respective secondary antibodies at RT for 1 hour. All samples were stained for nuclei with DAPI (1:5000) at RT for 3 minutes and mounted with FluorSave reagent (Merck). All image data of regenerated tissue were observed and collected using fluorescent microscopy (Olympus) and confocal microscopy (Leica).

Statistics.

Data were expressed as mean±standard error of the mean (SEM). Student's t-test was used for comparing two groups and one-way ANOVA was used for comparing multiple groups. Statistical significance was accepted when $p<0.05$.

TABLE 1

Conditions of inducing cell differentiation.

| Group name | Inducing factors |
| --- | --- |
| CNTF + T3 | 50 ng/ml CNTF and 10 ng/ml T3 |
| hIL12 | 100 ng/ml human IL12p80 |
| mIL12 | 100 ng/ml mouse IL12p80 |

TABLE 1-continued

Conditions of inducing cell differentiation.

| Group name | Inducing factors |
|---|---|
| CNTF + T3 + hIL12 | 50 ng/ml CNTF, 10 ng/ml T3 and 100 ng/ml human IL12p80 |
| CNTF + T3 + mIL12 | 50 ng/ml CNTF, 10 ng/ml T3 and 100 ng/ml mouse IL12p80 |

Results

Implantation of NSCs with Nerve Conduits Improves Functional Recovery of Sciatic Nerve Injury in Mice More than Conduits Only.

Figure 1:
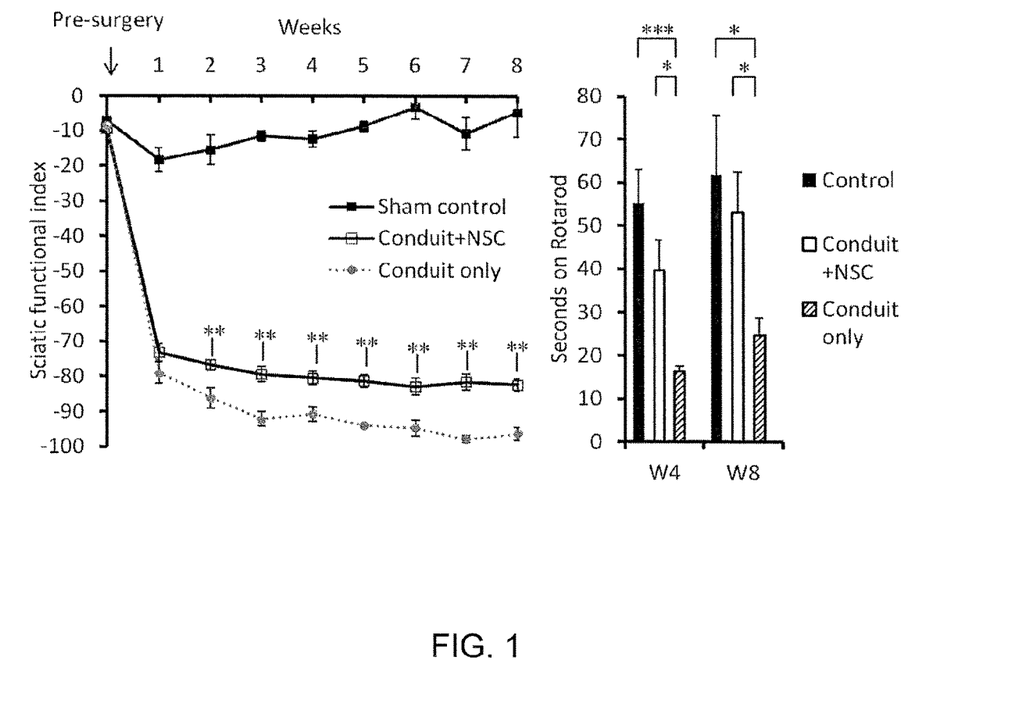
FIG. 1 is schematic diagrams illustrating the implantation of NSCs with nerve conduits improved functional recovery of sciatic nerve injury in mice more than conduits only. (A) SFI was used to assess functional recovery weekly from the first week to the eighth week. Statistical analyses indicated that the Conduit+NSC group had significantly better recovery than the Conduit only group. (B) The Rotarod test was done on the fourth and eighth week after surgery. The Conduit only group had significantly worse balance and walking on the Rotarod than the Control and Conduit+NSC groups. The Conduit+NSC group had better motor recovery and did not differ from the Control group. All data are presented as mean±standard error of the mean (SEM) (n=3 in Sham control group, n=8 in Conduit only group, n=8 in Conduit+NSC group, and n=8 at the fourth week and n=8 at the eighth week in the Control group). Statistical differences are indicated by *$p<0.05$ and **$p<0.01$.

After excision of left sciatic nerve (3 mm), all mice lost motor function at the left hindlimb, which showed the dragging walk phenotype with cringed toes. In this study, we implanted NSCs with conduit to repair the injured sciatic nerve. Functional recovery was assessed using non-invasive methods, Walking track analysis and the Rotarod test, during the period of regeneration. Sciatic functional index (SFI) is a calculated score of data from Walking track analysis that combines gait analysis and the temporal and spatial relationship of one footprint to another during walking. The SFI is on a scale from 0 to −100, where 0 corresponds to the normal walking function and −100 refers to the complete loss of function. In track analysis, sham control mice were defined as mice with the same surgical procedure but no actual damage of sciatic nerve. These mice showed no apparent difference in SFI score throughout the first week to eighth week after surgery when compared with the pre-surgery SFI score (FIG. 1A, Sham control). For the implantation of NSCs with conduit (FIG. 1A, Conduit+NSC group) or conduit only (FIG. 1A, Conduit only group), the SFI score showed no significant difference between the two groups (−73.2±2.5 vs. −77.0±3.9) at the first week after surgery. Beginning from the second week after surgery, the Conduit+NSC group showed a higher SFI score than the Conduit only group ($p<0.01$). The functional betterment in the Conduit+NSC group than the Conduit only group continued until the eighth week (FIG. 1A).

The Rotarod test is also used to assess the recovery of motor function and balance ability of injury sciatic nerve mice. In the Rotarod test, Control group mice were defined as without nerve dissection and muscle injury. The results of the Control group, Conduit+NSC group and Conduit only group in the Rotarod test at fourth week were 55±8, 40±7, and 16±1 s, and at eighth week were 62±14, 53±9, and 25±4 seconds, respectively (FIG. 1B). The Conduit only group showed a significantly reduced ability in balancing and walking on the Rotarod than the Control and Conduit+NSC group at the fourth and eighth week after surgery. Interestingly, no difference is observed in the Rotarod test between the Control and Conduit+NSC group at the fourth and eighth week after surgery. These results indicated that implantation of NSCs with conduit facilitated the functional recovery in sciatic nerve injury mice.

IL12p80 is Involved in NSCs-Mediated Sciatic Nerve Repair.

Figure 2:
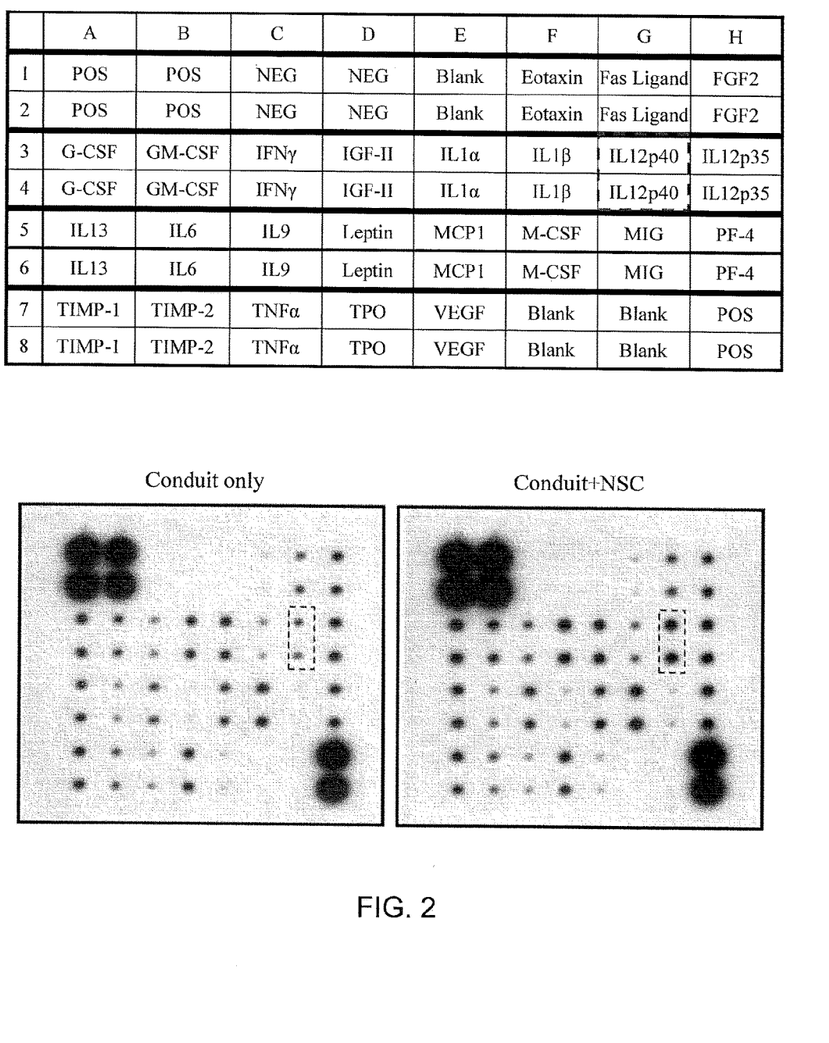
FIG. 2 is a table and photos illustrating the antibody array of cell extracts from implanted conduits with or without NSCs. The signal of IL12p40 (indicated by red dot square) existed in the cell extracts harvested from the Conduit+NSC group was 1.89-fold higher than the Conduit only group (n=4 in both Conduit only and Conduit+NSC group). These experiments were repeated three times and IL12p40 levels in the Conduit+NSC group were more greatly expressed than the Conduit only group.

NSCs hold the potential to differentiate into all three neuroectodermal lineages including Schwann cells, and may also secrete or recruit trophic factors for nerve regeneration (Ren Z. et al., Reviews in the Neurosciences 2012, 23:135-143). Therefore, to identify factors that were involved in NSCs-mediated nerve regeneration, the mouse antibody array is used to investigate the protein expression level between Conduit only and Conduit+NSC groups. Protein lysates extracted from the implanted nerve conduits with or without NSCs were harvested at the fourth week after surgery for protein antibody array. According to the quantification data of the antibody array, expression of IL12p40 in the cell extracts harvested from the Conduit+NSC group was 1.89-fold higher compared with the Conduit only group, yet expression of IL12p35 in the Conduit+NSC group was similar to (1.04-fold) the Conduit only group (FIG. 2, IL12p40 and IL12p35). IL12p40 was one of the subunits in IL12p70, and 20% to 40% of total IL12p40 subunit could be secreted as a homodimer form (IL12p80), which was 25-50-fold more active than IL12p40 monomer in the induction of biological function (Heinzel F. P. et al., *Journal of Immunology* 1997, 158:4381-4388; Gillessen S. et al., *European Journal of Immunology* 1995, 25:200-206; Jacobson N. G. et al., *Journal of Experimental Medicine* 1995, 181:1755-1762.) In the antibody array data, the Conduit+NSC group increased the expression levels of IL12p40 but not IL12p35, which indicated that IL12p80, the IL12p40 bioactive form, may be a factor involved in nerve regeneration. IL12p40 binds to IL12 receptor β1 and results in phosphorylation of Stat3 and activation of the Stat3 downstream signaling (Heinzel F. P. et al., *Journal of Immunology* 1997, 158:4381-4388; Gillessen S. et al., *European Journal of Immunology* 1995, 25:200-206; Jacobson N. G. et al., *Journal of Experimental Medicine* 1995, 181:1755-1762.). Previous studies indicate that Stat3 activation induces differentiation of neural progenitor cells into the astroglial lineage (Wang B. et al., *PLoS One* 2008, 3:e1856.). These results imply a role for IL12p80 in the activation of Stat3 downstream signaling and participation in nerve regeneration.

Implantation of NSCs with Conduit and IL12p80 Promotes Functional Recovery and Nerve Regeneration.

Figure 3:
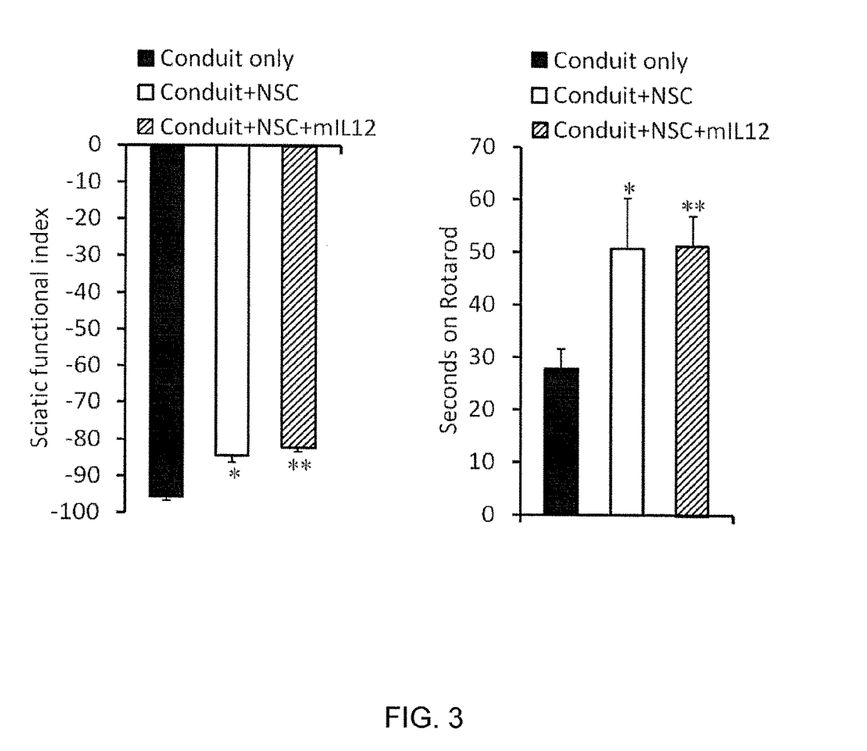
Figure 4:
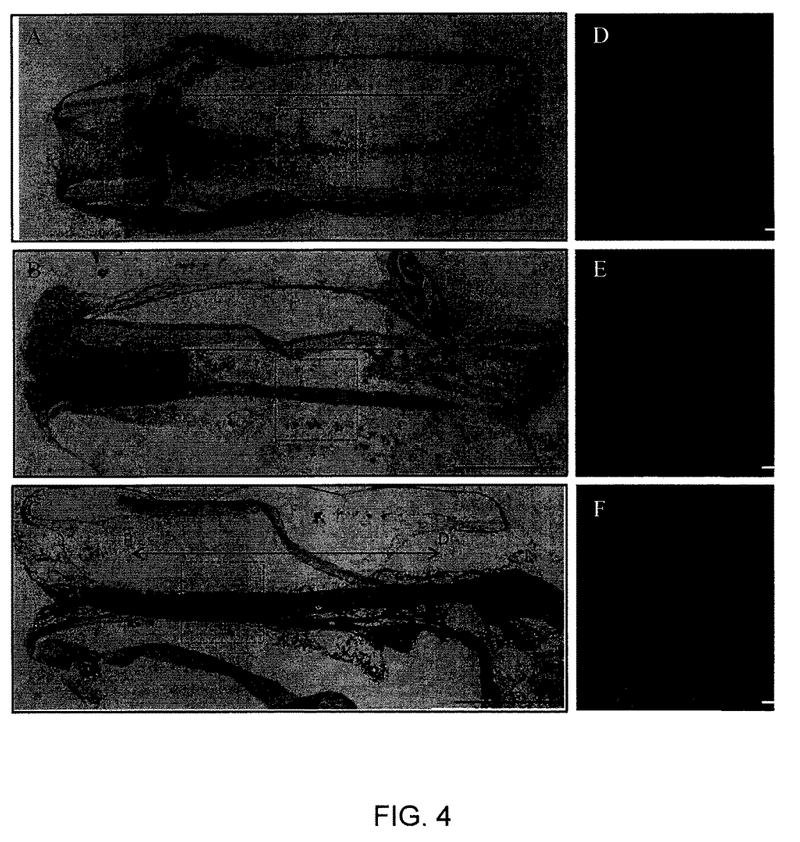
Figure 5:
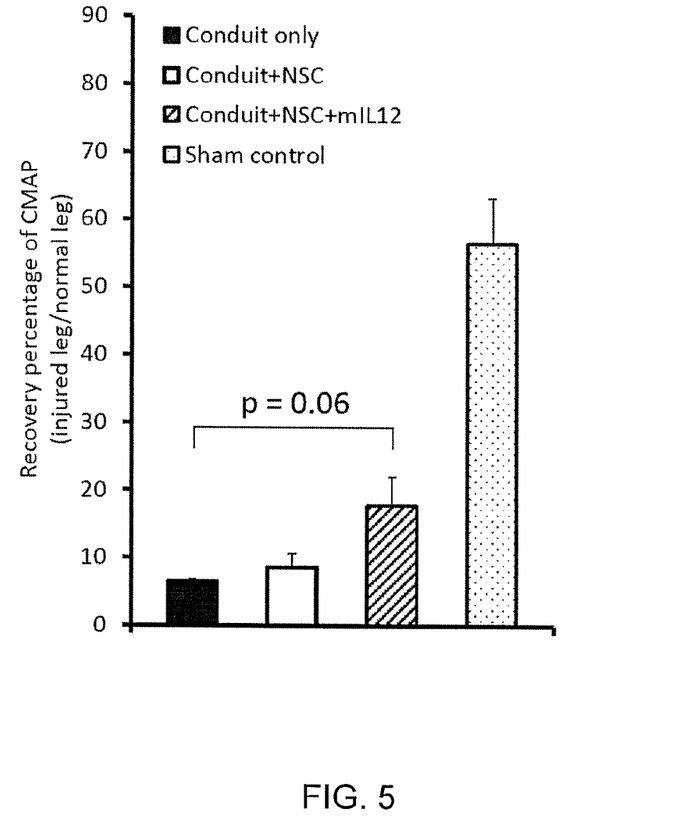
FIG. 5 is a schematic diagram illustrating recovery sciatic nerve injury measured in compound muscle action potential. The CMAPs of injured leg and contralateral normal leg were measured. The recovery of CMAP was calculated as injured leg divided by normal leg. The recovery of CMAP of different groups were shown (n=4 in the Conduit only group, n=4 in the Conduit+NSC group, n=6 in the Conduit+NSC+mIL12 group, and n=3 in the Sham control).

To test the function of IL12p80 in nerve regeneration, the sciatic nerve injury mice treated with the following conditions were compared: Conduit only group, conduit with NSCs (Conduit+NSC group), and conduit with NSCs and mouse IL12p80 (Conduit+NSC+mIL12 group). On the eighth week after implantation, functional assessment was performed by Walking track analysis and the Rotarod test. Mice of Conduit+NSC and Conduit+NSC+mIL12 group showed a significantly higher SFI score than the Conduit only group (FIG. 3A). In the Rotarod test, mice of the Conduit+NSC and Conduit+NSC+mIL12 group showed better walking and balancing abilities than the Conduit only group (FIG. 3B). Moreover, these data demonstrated that the Conduit+NSC+mIL12 group showed more significant results ($p<0.01$) than the group without IL12p80 ($p<0.05$) in functional assessment of both Walking track and Rotarod analyses (FIGS. 3A and 3B). However, the effect of additional administration with IL12p80 (Conduit+NSC+mIL12 group) was too feeble to discriminate the assisted ability of nerve repair from that without IL12p80 (Conduit+NSC group) in the functional assessments. Therefore, the effect of IL12p80 in nerve repair is demonstrated by histological section assessment (FIG. 4) and nerve conduction study (FIG. 5).

In the nerve regeneration study, 5 mm nerve conduit is implanted to connect the 3 mm sciatic nerve injury gap. The conduit sutured to the proximal and distal ends of injured sciatic nerve with 1 mm residual nerve on each end. Therefore, axons existed in the central region of the conduit were considered newly regenerated nerve. Axonal regeneration is observed by hematoxylin and eosin (H&E) staining, and immunohistochemistry using antibodies recognizing specific neural cell specific markers. In FIGS. 4A, 4B and 4C, "P" and "D" indicate the ends of residual nerve ("P" is 1.0 mm from proximal end of the implanted conduit and "D" is 3.0 mm distal from "P"). In H&E staining, Conduit+NSC (FIG. 4B) and Conduit+NSC+mIL12 (FIG. 4C) groups showed significant enhancement in the integration of regenerated axons compared with the Conduit only group (FIG. 4A). The status of nerve regeneration is further verified by using immunohistochemistry staining using anti-neurofilament 200 antibody (NF200, a marker of nerve fiber) and anti-protein zero antibody (PZO, a marker of myelinated Schwann cells). The immunohistochemical staining results demonstrated that the coupling of myelinated Schwann cells (PZO positive cell) with nerve fiber (NF200 positive cell) of regenerated nerve in the conduit (dotted line region in FIGS. 4A, 4B, and 4C, respectively) occurred in the Conduit+NSC (FIG. 4E) and to Conduit+NSC+mIL12 group (FIG. 4F), but not in the Conduit only group (FIG. 4D). Furthermore, the diameter of regenerative nerves is measured by reconstructing serial sample sections stained by H&E in Proximal, Medial, and Distal sites of implanted nerve conduits: Proximal site (1.0 mm from proximal end of conduit), Distal site (3.0 mm from the Proximal site), and Medial site (the center between the Proximal site and Distal site). At the Proximal and Distal sites, the diameter of regenerative nerve showed no significant difference among the three groups (262±44 µm, 284±42 µm, and 302±97 µm at Proximal sites and 279±56 µm, 298±75 µm, and 322±123 µm at Distal sites, respectively). In contrast, the diameter in the Medial site of the Conduit+NSC (189±18 µm) and Conduit+NSC+mIL12 (295±47 µm) groups were 2.9-fold and 4.5-fold thicker, respectively, than the Conduit only group (65±21 µm). Remarkably, in the Medial site of the regenerative sciatic nerve, the addition of IL12p80 increased the nerve diameter 1.6-fold compared with the group without IL12p80 (FIG. 4G). The schematic diagram of regeneration in the three groups is shown in FIG. 4H. Nerve conduction is measured by electrical stimulating the sciatic nerve and recording the compound muscle action potential (CMAP), which is the summated voltage response from individual muscle fiber action potential (Mallik A. et al., *J Neurol Neurosurg Psychiatry* 2005, 76 Suppl 2: ii23-31.). In the present application, the CMAPs of injured leg and contralateral normal leg were measured. The recovery percentage was calculated as the CMAP of injured leg normalized with the CMAP of contralateral normal leg (FIG. 5). The Conduit+NSC+mIL12 group showed better recovery status than either Conduit+NSC or Conduit only (17.7±4.3%, 8.5±2.1%, and 6.6±0.2%, respectively). Furthermore, the Conduit+NSC+mIL12 group showed lesser gastrocnemius muscle atrophy than Conduit only group (injured leg/normal leg was 0.39±0.02 and 0.26±0.07, respectively, p<0.01). These data demonstrated that implantation of NSCs with conduits facilitated the functional recovery and nerve regeneration. Importantly, additional administration of IL12p80 showed statistically significant results in the functional assessment of both SFI and Rotarod analyses, improvement of nerve conduction, and increase of the diameter of newly regenerated nerves.

IL12p80 Stimulates Differentiation of Mouse NSCs to the Oligodendrocyte and Schwann Cell Lineages.

Figure 6:
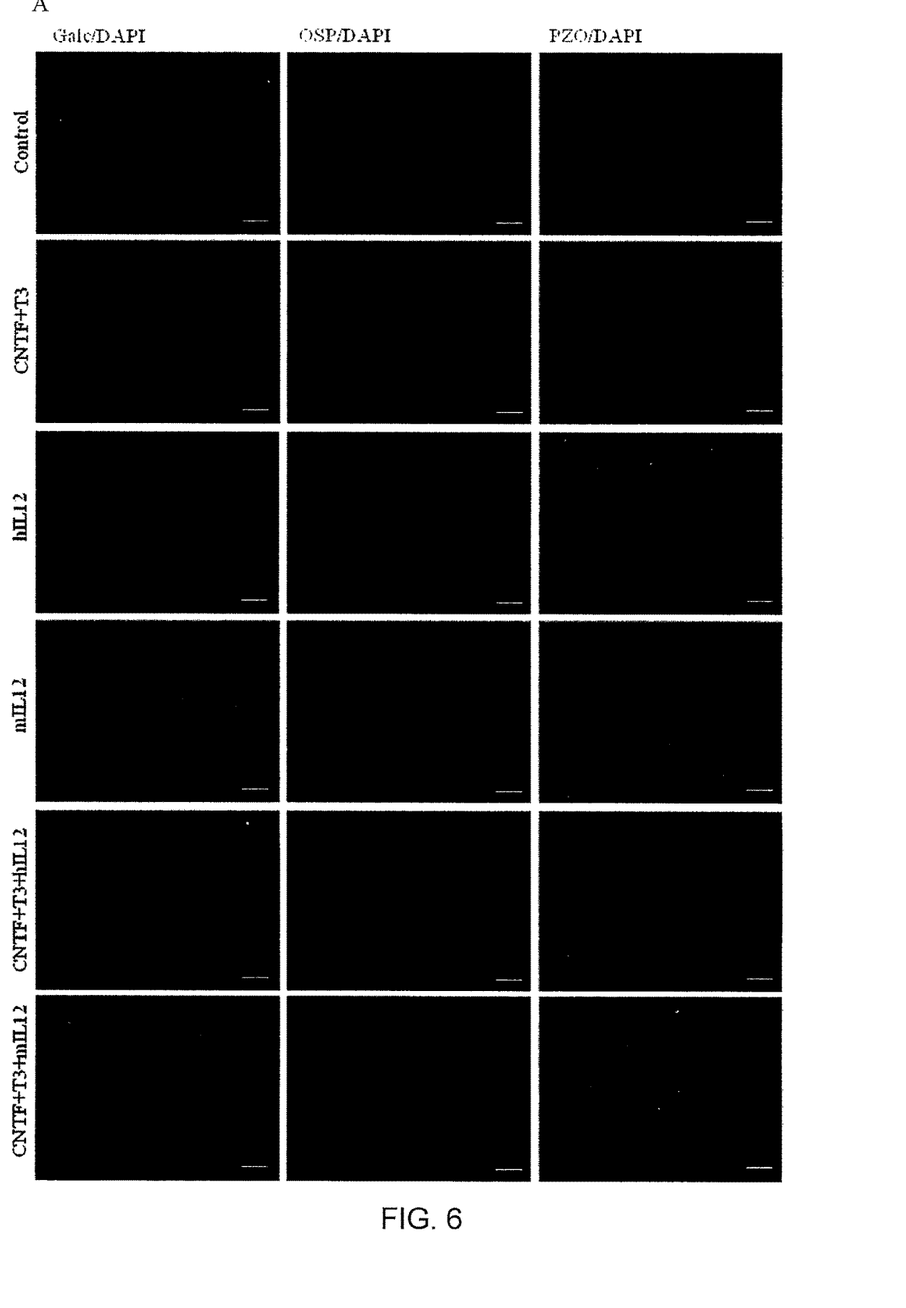
FIG. 6 illustrates the immunocytochemistry results showing that IL12p80 could replace CNTF+T3 to induce oligodendrocyte differentiation of mouse NSCs. (A) Mouse NSCs were induced to differentiate into oligodendrocytes using CNTF+T3 or IL12p80 (listed in Y axis). Differentiated cells were stained with oligodendrocyte markers: anti-Galc antibody and anti-OSP antibody, or myelinated Schwann cell marker: anti-PZO antibody (listed in X axis). The folds of marker-positive cells were quantified and summarized in (B). Scale bar in each graph is 100 µm. Statistical differences are shown as *p<0.05 and **p<0.01.
Figure 7:
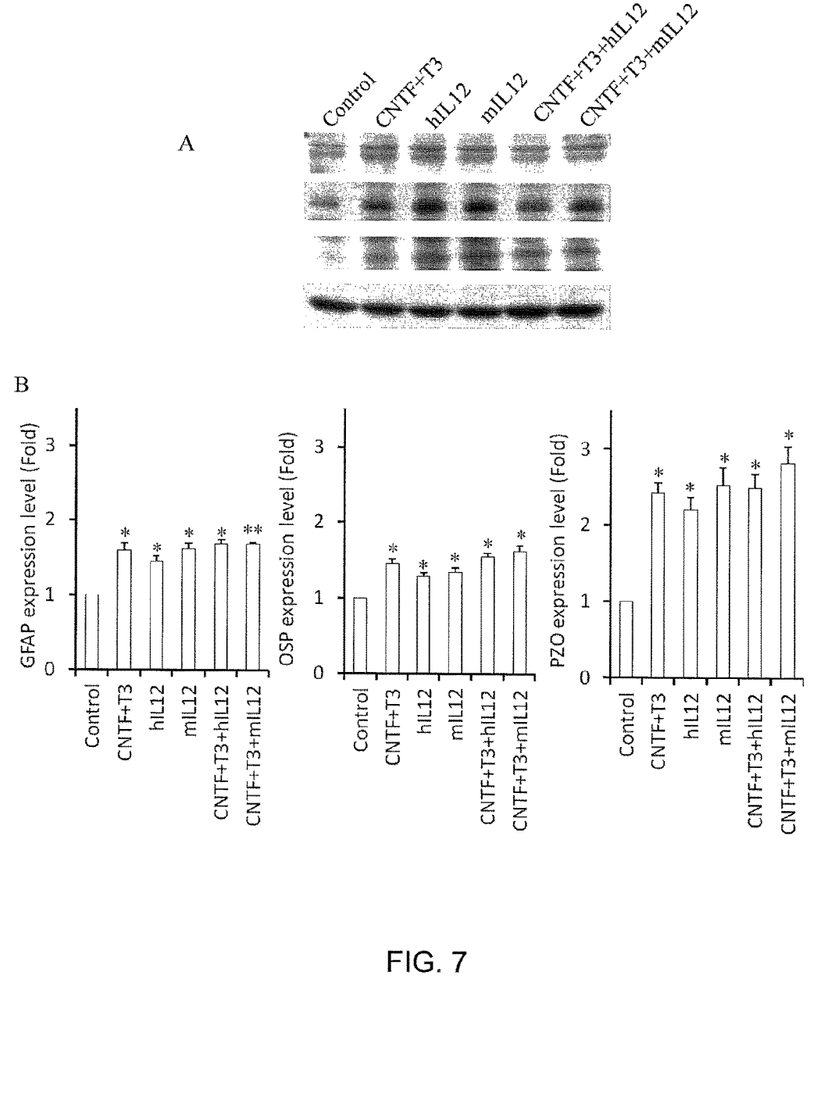
FIG. 7 illustrates the western blotting results showing that IL12p80 could differentiate mouse NSCs to oligodendrocytes and Schwann cells. Mouse NSCs were induced to differentiate into oligodendrocytes using CNTF+T3 or IL12p80. Differentiation groups were named by different cytokine treating conditions. Cell differentiation was characterized using Western blotting with lineage specific antibody against astroglial marker GFAP, oligodendrocyte marker OSP, and myelinated Schwann cell marker PZO (A). The quantification results are shown in (B). Statistical differences are shown as *p<0.05 and **p<0.01.

The present application then studied the potential of IL12p80 in inducing oligodendrocyte and Schwann cell differentiation in mouse NSCs. Cells dissociated from neurospheres were cultured in DMEM/F12 supplemented with 2% FBS as differentiation control medium (Control group), and oligodendrocyte differentiation medium (CNTF+T3 group), respectively (Hsu Y. C. et al., *Developmental Dynamics* 2009, 238:302-314; Lee D. C. et al, *Molecular and Cellular Neurosciences* 2009, 41:348-363.). To test the potential of IL12p80 in triggering oligodendrocyte and Schwann cell differentiation, 100 ng/ml human IL12p80 (hIL12p80) or mouse IL12p80 (mIL12p80) were added to the control group or CNTF+T3 group and named hIL12, mIL12, CNTF+T3+hIL12, and CNTF+T3+mIL12 groups. The differentiated cells were verified using immunofluorescence staining with primary antibody recognizing specific cell markers: galactocerebroside (Galc; oligodendrocyte), oligodendrocyte specific protein (OSP; oligodendrocyte), and myelin protein zero (PZO; myelinated Schwann cells), and fluorescent dye conjugated secondary antibodies (FIG. 6A). The percentage of marker positive cells are quantified and summarized in FIG. 6B. Cell morphology and immunofluorescence staining results showed that IL12p80 could replace CNTF+T3 for inducing oligodendrocyte or myelinated Schwann cells differentiation in mouse NSCs. The cell differentiation and maturation status are verified by Western blotting using lineage specific antibodies against glial fibrillary acidic protein (GFAP, astroglia marker), OSP, and PZO (FIG. 7A), respectively. The quantification result showed that protein levels of GFAP, OSP and PZO were upregulated in the differentiation conditions containing IL12p80 (FIG. 7B). These results demonstrated that IL12p80 could induce NSCs to differentiate into oligodendrocytes and myelinated Schwann cells.

IL12p80 Induces Phosphorylation of Stat3 in NSCs

Figure 8:
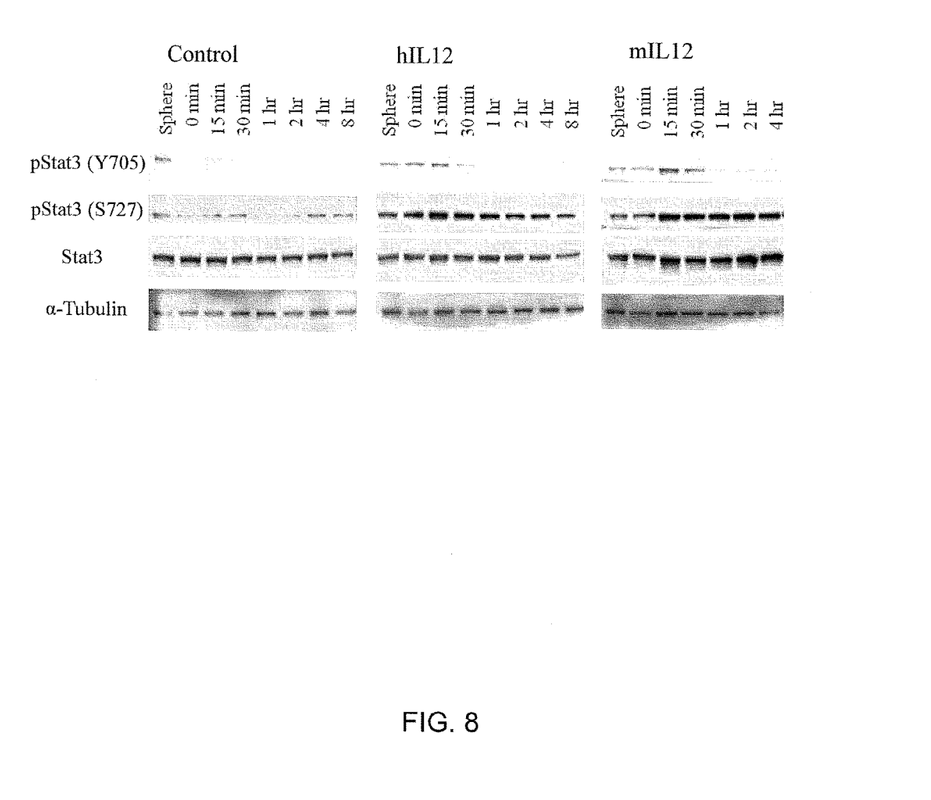

In NSCs, Stat3 phosphorylation has been shown to participate in oligodendrocyte differentiation processes (Wang B. et al., *PLoS One* 2008, 3:e1856.). In T cells, IL12p40 subunit can bind to IL12 receptor β1 and then induce Stat3 phosphorylation and the downstream signaling pathway (Jacobson N. G. et al., *Journal of Experimental Medicine* 1995, 181:1755-1762.). Therefore, IL12p80 could trigger oligodendrocyte differentiation in NSCs through Stat3 activation. The phosphorylation status of Stat3 in hIL12p80 or mIL12p80 treated NSCs is analyzed by using Western blotting. In this study, the phosphorylation status of both Y705 and S727 (Stat3 phosphorylation sites) were slightly expressed in neurospheres (FIG. 8, lanes of Sphere). Both human and mouse IL12p80 induced phosphorylation of Stat3 at Y705; the intensity peaked at 15 minutes, and began to decline at 30 minutes. Similarly, phosphorylation of Stat3 at S727 was increased by IL12p80 and sustained for 8 hours (FIG. 8, hIL12 group, and mIL12 group). These results revealed that Stat3 phosphorylation was crucial for IL12p80-induced oligodendrocyte differentiation in NSCs.

CONCLUSION

In this study, it is demonstrated that implantation of IL12p80 along with NSCs in nerve conduits improves motor function recovery, promotes nerve regeneration, improves nerve conduction, and increases the diameter of newly regenerated nerve. The regenerated nerve from the Conduit+NSC+IL12 is up to 4.5 fold thicker than the Conduit only group at the medial section of the injured nerve. IL12p80 could induce NSCs to differentiate into oligodendrocytes or myelinated Schwann cells in vitro. It is further showed that the induction of differentiation may be through the phosphorylation of Stat3. The administering of IL12p80 alone could achieve a certain degree of neural repair.

DISCUSSION

IL12p80 is a homodimer of IL12p40, while IL12p70 is a heterdimer of IL12p40 and IL12p35. IL12p40 binds to IL12 receptor β1 and IL12p35 binds to IL12 receptor β2. It was also reported that IL23 is a heterodimer of IL12p40 and IL23p19, with IL23p19 binding to the IL23 receptor. It has been shown that IL12p80 along with NSCs in nerve conduits improves nerve injury repair. The administering of IL12p80 alone could achieve a certain degree of neural repair.

It has been shown that IL12p70 could enhance the neurite out growth of mouse sympathetic superior cervical ganglion neurons in vitro (Lin H. et al., *Neurosci. Lett.* 2000, 278: 129-132.). Therefore, proteins that contain IL12p40 subunit, including IL12p80, IL12p70, and IL23 could all contribute to neural repair. The scope of neural repair could include not only neurogenesis of nerve injuries, such as peripheral nerve injury, spinal cord injury and stroke, but also neurodegenerative diseases such as Alzheimer's disease, Parkinson's disease and multiple sclerosis (Beckervordersandforth R. et al., *Stem Cell Reports* 2014, 2:153-162.).

Realizations of the composition and methods to enhance nerve regeneration utilizing neural stem cells and IL12p40 have been described in the context of particular embodiments. These embodiments are meant to be illustrative and not limiting. Many variations, modifications, additions, and improvements are possible. These and other variations, modifications, additions, and improvements may fall within the scope of the invention as defined in the claims that follow.

What is claimed is:

1. A method for regenerating nerve, comprising administering a nerve conduit containing a nerve regeneration composition to a subject, wherein the nerve regeneration composition comprises a homodimer of interleukin-12 subunit p40 (IL12p40).

2. The method of claim 1, wherein the subject is a mammalian.

3. The method of claim 1, wherein the nerve conduit containing the nerve regeneration composition is provided by injection, implantation, and/or transdermal route.

4. The method of claim 1, wherein the nerve conduit containing the nerve regeneration composition is implanted in a target nerve or a tissue around the target nerve.

5. The method of claim 1, wherein nerve regeneration composition further comprises neural stem cells (NSCs).

* * * * *